United States Patent
Hiller et al.

(10) Patent No.: US 7,896,873 B2
(45) Date of Patent: Mar. 1, 2011

(54) ELECTRODE CATHETER FOR THE ELECTROTHERAPY OF CARDIAC TISSUE

(75) Inventors: Karl-Heinz Hiller, Gochscheim (DE); Matthias Nahrendorf, Veitsheim (DE); Wolfgang Bauer, Kitzingen (DE)

(73) Assignee: Biotronik CRM Patent AG (CH)

( * ) Notice: Subject to any disclaimer, the term of this patent is extended or adjusted under 35 U.S.C. 154(b) by 1275 days.

(21) Appl. No.: 10/596,091

(22) PCT Filed: Dec. 1, 2004

(86) PCT No.: PCT/EP2004/013857
§ 371 (c)(1),
(2), (4) Date: May 30, 2006

(87) PCT Pub. No.: WO2005/053555
PCT Pub. Date: Jun. 16, 2005

(65) Prior Publication Data
US 2007/0100232 A1 May 3, 2007

(30) Foreign Application Priority Data

Dec. 1, 2003 (DE) .................................. 103 56 640
Mar. 1, 2004 (DE) .......................... 10 2004 010 424

(51) Int. Cl.
*A61B 18/14* (2006.01)
*A61B 5/042* (2006.01)
*A61N 1/05* (2006.01)
(52) U.S. Cl. ........................... 606/41; 600/374; 607/116
(58) Field of Classification Search .................. 600/373, 600/374, 381; 606/41; 607/116
See application file for complete search history.

(56) References Cited

U.S. PATENT DOCUMENTS

| 4,102,331 A | * | 7/1978 | Grayzel et al. ................ 600/385 |
| 4,467,817 A | * | 8/1984 | Harris ........................... 607/122 |
| 4,585,013 A |   | 4/1986 | Harris |
| 4,721,118 A |   | 1/1988 | Harris |
| 5,336,254 A |   | 8/1994 | Brennen et al. |
| 5,413,089 A | * | 5/1995 | Andors et al. .................. 126/77 |
| 5,433,730 A | * | 7/1995 | Alt ..................................... 607/5 |
| 5,523,534 A | * | 6/1996 | Meister et al. ................. 174/36 |
| 6,032,063 A |   | 2/2000 | Hoar et al. |
| 6,592,581 B2 | * | 7/2003 | Bowe .............................. 606/41 |
| 7,142,903 B2 | * | 11/2006 | Rodriguez et al. ............ 600/374 |
| 7,272,427 B2 | * | 9/2007 | Ristolainen ................... 600/372 |
| 2004/0111141 A1 | * | 6/2004 | Brabec et al. ................ 607/119 |

FOREIGN PATENT DOCUMENTS

| WO | WO 0197688 | 12/2001 |
| WO | WO 02087676 | 11/2002 |

* cited by examiner

*Primary Examiner* — Lee S Cohen
(74) *Attorney, Agent, or Firm* — Craig A. Fieschko, Esq.; DeWitt Ross & Stevens S.C.

(57) ABSTRACT

The present invention relates to an electrode catheter for defibrillation, mapping or ablation of cardiac tissue. Said catheter comprises a terminal (40) on the proximal end of the electrode catheter and one or more sensing and/or treatment electrodes (14, 16) that are situated on or in the vicinity of the distal end of the electrode catheter, in addition to at least one electric conductor (44, 62), which is used to electrically connect a respective sensing or treatment electrode to the terminal. The electric conductor (44, 62) is composed of carbon and the electrode catheter is configured to be suitable for us as part of magnetic resonance tomography and for connection to electrophysiotherapy equipment. Said catheter comprises at least one defibrillation electrode, or at least one sensing electrode (14, 16) for the recording and evaluation of cardiac tissue potentials, or at least one treatment electrode (14) for delivering high-frequency currents for ablation purposes.

20 Claims, 5 Drawing Sheets

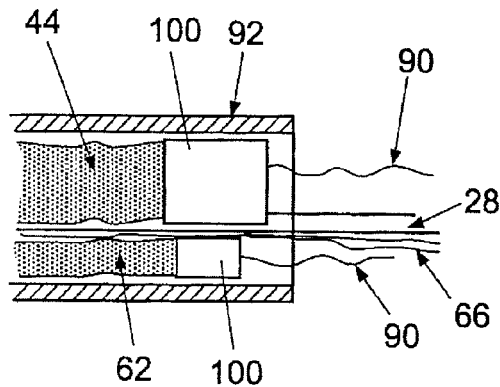
Fig.5c
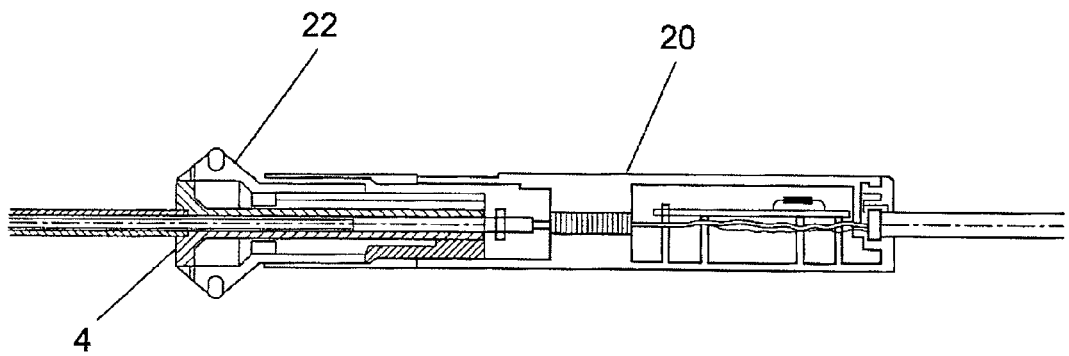
Fig.5d
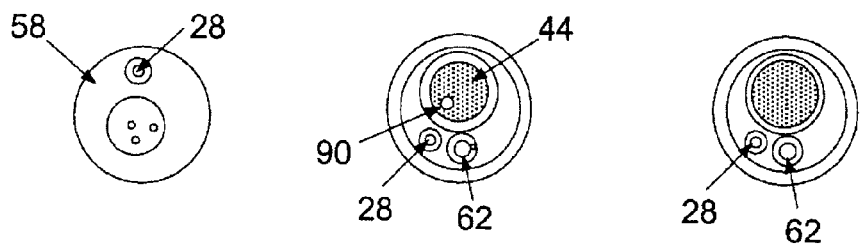
B-B
Fig.5e
C-C
Fig.5f
D-D
Fig.5g

ELECTRODE CATHETER FOR THE ELECTROTHERAPY OF CARDIAC TISSUE

FIELD OF THE INVENTION

The present invention relates to an electric catheter for the electrotherapy or examination of cardiac tissue, i.e., of myocardium.

BACKGROUND OF THE INVENTION

The present invention relates to an electric catheter for the electrotherapy or examination of cardiac tissue, i.e., of myocardium. On its proximal end, the electrode catheter has a terminal, using which the electrode line is connected to an electrical generator, an electrotherapy device, or even to an implant, such as a cardiac pacemaker or defibrillator. The therapy device is preferably a generator for high-frequency current for tissue ablation. On its distal end, the electrode catheter has one or more sensing electrodes or, additionally or alternatively, treatment electrodes.

Electrode catheters of this type are known in particular in the field of electric physiology for detecting and treating stimulus conduction malfunctions in the heart and are also referred to as EP catheters (electrophysiology catheters). In the present case, this name is to include both mapping catheters for detecting myocardial stimulus conduction or ablation catheters for the local erosion of cardiac tissue (myocardium) or combinations of such electrode catheters. Such electrode catheters are used for the purpose of detecting the excitation propagation in the myocardium with the aid of sensing electrodes in a first step, in order to be able to recognize malfunctions of the excitation propagation in this way. Subsequently, by applying typically high-frequency AC current, which may be output in a targeted way via treatment electrodes, tissue erosion (ablation) may be caused, with the result that stimulus conduction no longer occurs where the cardiac tissue is eroded.

Corresponding catheters and treatments are known in principle and have had the great disadvantage up to this point that the treatment cannot be performed under observation in the course of magnetic resonance tomography, since the electrical lines between the proximal end of the electrode catheter and the electrodes at the distal end of the electrode catheter may heat up significantly as a result of induction currents induced by the magnetic resonance tomography. In addition, the electrical conductors of the typical electrode catheters result in undesired artifacts in the image recorded using magnetic resonance tomography.

This problem is all the greater since the maximum power consumption of the electrical lines is given when their length is a multiple of half of the wavelength output by the magnetic resonance tomograph, i.e., $$\frac{\lambda}{2}.$$

This condition is fulfilled in typical electrical lines of typical EP catheters. A further difficulty is that the greatest heating occurs precisely in proximity to the distal end of the corresponding electrode catheter in the area between endocardium and myocardium.

Up to this point, these reasons have resulted in electrophysiological examination of the myocardium or electrotherapy of the myocardium in the form of ablation or similar treatments not being able to be performed under observation in magnetic resonance tomographs.

Similar problems also result in connection with stimulation electrode catheters or defibrillation electrode catheters for connection to an implantable cardiac pacemaker, cardioverter, defibrillator, or the like. Since typical defibrillation and stimulation electrode catheters are not compatible with magnetic resonance, the patients having such implants may not be examined using a magnetic resonance tomograph.

The object of the present invention is therefore to provide an electrode catheter which also allows use in magnetic resonance tomographs.

This object is achieved according to the present invention by an electrode catheter of the type cited at the beginning, in which the electrical conductor(s) running from the proximal to the distal ends of the electrode catheter is/are made of carbon.

It has been shown that, using electrical conductors made of carbon, both the undesired effect of heating of the electrical conductors because of alternating magnetic fields in the currents induced in magnetic resonance tomographs and also the undesired effect of artifacts in magnetic resonance tomographs may be avoided.

Interestingly, electrode catheters for connection to a cardiac pacemaker are known from each of US patents U.S. Pat. Nos. 4,467,817, 4,721,118 and 4,585,013, in which the electrical conductors between the proximal end connected to the cardiac pacemaker and the distal end located in the heart are made of carbon fibers, which are provided in the form of a bundle in a multiple of approximately 3000 high modulus filaments. These electrode catheters are to achieve the object of providing an electrode catheter having the smallest possible diameter. There is no indication in the publications that electrode catheters for electrophysiology, in particular ablation electrode catheters, may be constructed similarly, or that electrode catheters having an electrical conductor made of carbon fibers permit use or observation in the framework of magnetic resonance tomography.

SUMMARY OF THE INVENTION

An essential aspect of the present invention is thus the recognition that electrode catheters whose electrical conductors are made of carbon also allow use in the framework of magnetic resonance tomography.

A further recognition on which the present invention is based is that the use of electrical conductors made of carbon is especially suitable for electrode catheters for use in the framework of electrophysiology.

Such electrode catheters differ from stimulation electrode catheters for connection to a cardiac pacemaker in that the number of electrodes which the electrode catheter carries in the area of its distal end is, in electrode catheters for electrophysiology, typically a multiple of the number of electrodes which a cardiac pacemaker electrode has. These multiple electrodes of a typical electrode catheter for electrophysiology are additionally electrically connected via a corresponding number of electrical conductors to the proximal end of the electrode line. In contrast, a cardiac pacemaker electrode typically has precisely two electrodes in the area of the distal end if the electrode catheter is implemented as a bipolar electrode catheter. This is also required for ablation to transmit larger amounts of energy via the electrode line than is the case for cardiac pacemaker electrodes.

Typically, electrode catheters for ablation—i.e., ablation catheters, are implemented as controllable in such a way that a distal end section of the electrode catheter—i.e., the catheter shaft—may be laterally deflected using a control handle attached to the proximal end of the electrode line. Electrode catheters considered for permanent implantation for connection to a cardiac pacemaker or defibrillator do not have this feature.

In accordance with the intended use as an electrode catheter for electrophysiology, a preferred embodiment variation of the electrode catheter has multiple ablation electrodes or multiple sensing electrodes or both. These electrodes are each electrically connected via a separate electrical conductor to a terminal on the proximal end of the electrode line.

An alternative electrode catheter implemented for connection to an implantable defibrillator has at least one defibrillation electrode. Defibrillation electrodes differ from typical stimulation or sensing electrodes, as are connected to a cardiac pacemaker, through their typically significantly larger spatial dimensions, which provide a sufficiently large electrode surface to limit the current density at the typical current strengths required for defibrillation to an amount at which tissue injuries are avoided.

In all embodiment variations, the electrode catheter according to the present invention is constructed from materials compatible with magnetic resonance.

The terms compatible with magnetic resonance and compatible with nuclear magnetic resonance are used as synonyms here.

The material forming the electrical conductor, which is compatible with magnetic resonance, is carbon, which is provided in the form of carbon fibers, which comprise multiple individual elements, in a preferred embodiment variation of the present invention.

The electrical conductor is preferably enclosed by an insulating envelope made of a flexible plastic which is compatible with magnetic resonance. This plastic may be made partially or completely of silicone, for example.

The insulating envelope preferably contains an x-ray contrast agent, since neither the electrical conductor made of carbon nor an insulating envelope made of silicone, for example, results in sufficient contrast in an x-ray image. The x-ray contrast agent may contain barium sulfate or metal particles, for example. The distribution of the metal particles within an insulating plastic matrix is preferably selected in this case in such way that it does not influence the magnetic resonance compatibility and at most results in slight artifacts in the framework of the magnetic resonance tomography.

In order that the electrical conductors of the electrode catheter have the desired electrical properties, these preferably have cross-section between 0.5 and 1.5 mm and a length between 40 cm and 120 cm. In preferred embodiment variations, smaller cross-sections correspond to shorter lengths and larger cross-sections correspond to greater lengths in this case.

Further preferred embodiment features or independent ideas of the present invention which may be the subjects of claims that have not been formulated until now are cited in the following.

One aspect, which is also independently protectable, relates to the connection of a metallic electrical conductor, such as a copper wire, to an electrical conductor made of carbon fibers.

One connection variation is that one end of the metallic conductor is situated overlapping the carbon fibers of the electrical conductor made of carbon fibers and the metallic conductor and the conductor made of carbon fibers are frictionally connected using a crimp sleeve. Overlapping of this type may be produced by pushing one end of the metallic conductor in the longitudinal direction into the initially loose fiber bundle which the electrical conductor made of carbon fibers forms, so that the corresponding end of the electrical conductor is completely enclosed by carbon fibers.

An alternative connection variation, which is also capable of independent protection, is that a sleeve is squeezed (crimped) or glued using an electrically conductive adhesive onto a particular end of electrical conductor made of carbon fibers and this sleeve is connected to a continuing electrical conductor through soldering or welding. Alternatively, the end of an electrical conductor made of carbon fibers may also be glued directly to a metallic conductor.

A further aspect of the present invention which is capable of independent protection, in particular in connection with controllable ablation or mapping catheters, is that the electrical conductor between a particular electrode and the proximal end of the corresponding electrode catheter is not made of carbon fibers over its entire length. Rather, the electrical conductor may be formed in a short longitudinal section of the electrode catheter—preferably in a longitudinal section intended for lateral deflection—by typical metallic conductors, such as copper wires, which are then connected in the way described above with the electrical conductor made of carbon fibers. If the length of these metallic electrical conductors is selected so it is shorter than one fourth of the wavelength of the magnetic alternating field, there is hardly any heating of this metallic conductor in spite of the use of a metallic conductor, since the length of the metallic conductor is not tuned to the wavelength of the magnetic alternating field.

An especially preferred variation of a controllable ablation or mapping catheter is that a distal longitudinal section of a particular electrical conductor, which runs inside a flexible catheter section, is made of a metallic conductor, preferably a copper wire, while the longitudinal section of the conductor in a proximal, stiffer catheter section is made of carbon.

The variations of the electrode catheter discussed here, having an electrical conductor which has one longitudinal section made of a metallic conductor and another longitudinal section made of an electrical conductor made of carbon fibers, as well as the variations of the connection of an electrical conductor made of carbon fibers to a metallic electrical conductor discussed here, represent features which may be implemented not only in catheters, such as mapping catheters or ablation catheters, but rather may also be provided in electrode catheters, such as stimulation electrode catheters or defibrillation electrode catheters for connection to implantable medical devices.

Electrode catheters of this type, regardless of whether they are implemented as defibrillation electrodes for connection to an implantable defibrillator or as electrophysiology catheters, i.e., as mapping or ablation catheters, allow the performance of novel methods, previously unknown methods, or methods considered impossible to perform.

These methods include methods for electrotherapy of the heart, in which electrotherapy is performed during magnetic resonance tomography, which is made possible by using an electrode catheter that is constructed as compatible with magnetic resonance by using an electrical conductor made of carbon.

Electrotherapy of this type preferably comprises tissue erosion (ablation) of the heart through delivery of high-frequency current to the cardiac tissue.

Alternatively or additionally, the electrotherapy may also comprise electrostimulation of the cardiac tissue.

Furthermore, electrode catheters which are constructed as compatible with magnetic resonance by using an electrical conductor made of carbon also allow currently unknown methods and methods which are considered impossible to perform for detecting electrical potentials of cardiac tissue, in which these potentials are recorded during magnetic resonance tomography using electrodes situated intercardially, the electrodes being electrically connected via electrical conductors made of carbon to a proximal end of the electrode catheter.

In all cases described here, the electrodes themselves may be metallic or may also be made of carbon. Electrodes of this type and the basic construction of electrodes for defibrillation or for electrophysiology are known in principle in regard to the design of the electrodes and the external construction of the electrode catheter. The decisive difference between electrophysiology catheters or defibrillation electrode catheters known per se and the electrode catheter according to the present invention is the construction of the electrical conductors, which are made of metal wires or metal coils in typical electrode catheters, for example, while these conductors are made of carbon in the electrode catheters according to the present invention.

In the following, an electrophysiology catheter according to the present invention is to be described as an example on the basis of the ablation catheter variations shown in the figures.

DETAILED DESCRIPTION OF PREFERRED VERSIONS OF THE INVENTION

Figure 1:
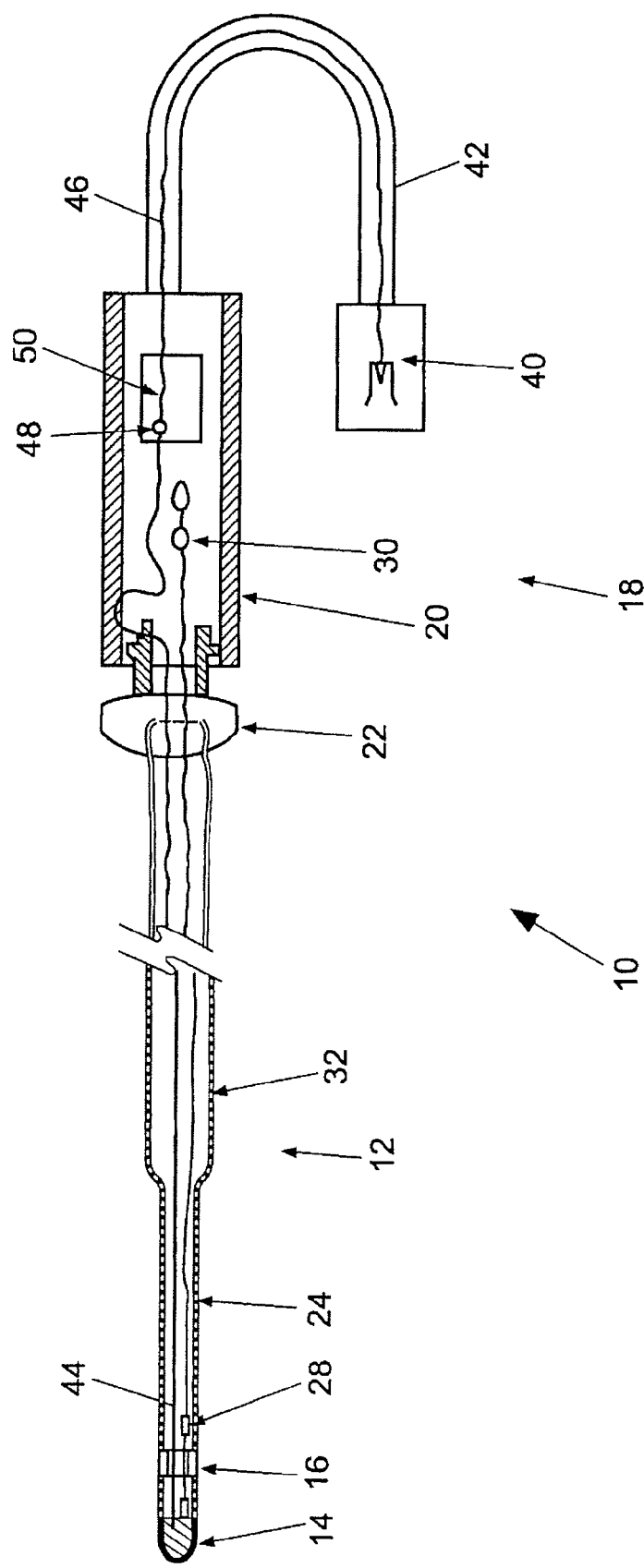
FIG. 1: shows a schematic sketch of a controllable, bipolar ablation catheter.

The ablation catheter 10 illustrated in FIG. 1 has a catheter shaft 12, which is also identified as an electrode catheter 12 in the framework of this description and the claims. The electrode catheter 12 carries two electrodes on its distal end, namely a tip electrode 14 and a ring electrode 16. The tip electrode 14 and the ring electrode 16 are used in the case of tissue erosion (ablation) for delivering high-frequency AC current to surrounding tissue in order to heat the tissue using the AC current enough that it erodes.

At the proximal end, the electrode catheter 12 is connected to a handle 18, which has a holding part 20 and a displacement part 22. Holding part 20 and displacement part 22 are displaceable in relation to one another in a known way in the longitudinal direction of the holding part 20 in order to cause lateral deflection of a distal end section 24 of the electrode catheter 12. This is performed in a way known in principle with the aid of a control wire 28 guided in a lumen 26 (see FIG. 3) of the electrode catheter 12, which is attached in the area of the distal end of the electrode catheter 12. Proximal to this attachment point, the control wire 28 is guided so it is longitudinally displaceable in the lumen 26 and solidly connected to the holding part 20 via a crimp connection 30, while the proximal end of the electrode catheter 12 is also connected to the displacement part 22. In this way known to those skilled in the art, with the aid of the holding part 20 of the displacement part 22, a relative displacement of the control wire 28 in relation to the remaining electrode catheter 12 may be produced, which results in a corresponding lateral deflection of the distal end section 24 of the electrode catheter 12 because of the eccentric arrangement of the control wire 28 in relation to the cross-section of the electrode catheter 12. This form of controllability is a feature of typical ablation catheters known to those skilled in the art.

In order that a lateral deflection of the distal end section 24 of the electrode catheter is restricted to this distal end section 24, the distal end section 24 is constructed as more flexible than an adjoining proximal shaft section 32 of the electrode catheter 12. The proximal shaft section is reinforced by a braid.

As noted, the electrodes 14 and 16 are used for delivering high-frequency AC current or ablation or also for sensing electrical potentials of the cardiac tissue, i.e., mapping. For both purposes, the electrodes 14 and 16 have to be electrically connected to a terminal 40, which is connected via a cable 42 to the handle 18.

The electrical connection between the particular electrodes 14 or 16 and the terminal 40 is described in the following solely for the electrical connection between the tip electrode 14 and the terminal 40 as an example. The electrical connection between the ring electrode 16 and the terminal 40 is designed correspondingly.

The tip electrode 14 is connected via an electrical conductor 42 made of carbon fibers to a typical electrical conductor 46 of the cable 42. The electrical conductor 44 made of carbon fibers extends from the tip electrode 14 up to a connection point within the holding part 20, which is made of a crimp sleeve 48 pushed onto the proximal end of the electrical conductor 44 made of carbon fibers and a small circuit board 50.

The crimp sleeve 48 is connected in a known way by squeezing to the proximal end of the electrical conductor 44 made of carbon fibers. In addition, the crimp sleeve 48 is soldered to a printed conductor in the circuit board 50 or welded to this printed conductor. In the same way, the typical electrical conductor 46 is connected to the same printed conductor of the circuit board 50.

The electrical connection between the tip electrode 14 and the distal end of the electrical conductor 44 made of carbon fibers is constructed as follows: a distal crimp sleeve 52 is squeezed onto the distal end of the electrical conductor 44. This metallic distal crimp sleeve 52 is electrically connected via a soldered or welded connection 54 to the cap-shaped tip electrode 14.

Figure 3:
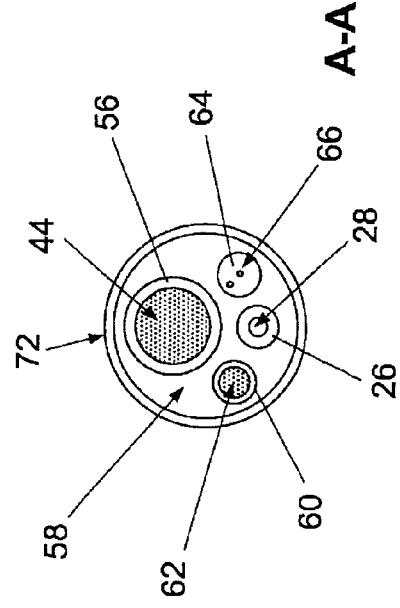
FIG. 3: shows a cross-section through the distal end of the ablation catheter from FIG. 1, at the point identified in FIG. 2.

As may be seen from the cross-section A-A shown in FIG. 3, the electrical conductor 44 made of carbon fibers is guided in a further lumen 56 of a multi-lumen hose 58. This multi-lumen hose 58 extends between the distal end and the proximal end of the electrode catheter 12. The multi-lumen hose 58 is manufactured from flexible, electrically insulating plastic. A suitable plastic is silicone, for example. In addition to the lumens 26 and 56 already noted for the control wire 28 and the electrical conductor 44 made of carbon fibers, respectively, the multi-lumen hose 58 has two further lumens, namely a lumen 60 in which a further electrical conductor 62 made of carbon fibers is guided, which is used for contacting the ring electrode 16 and has a smaller diameter than the electrical conductor 44 for contacting the tip electrode 14.

A fourth lumen 64 is used for receiving two electrical conductors or two optical fibers 66, which lead to the temperature sensor 68, which is situated in a cavity in the distal end of the tip electrode 14. With the aid of the temperature sensor 68, tissue ablation may be performed in way known per se with temperature control. The temperature sensor 68 is connected using an electrically insulating, but heat conducting adhesive 70 to the tip electrode 14. For reasons of magnetic resonance compatibility, the temperature sensor 68 is preferably an optical temperature sensor which is connected via two optical fibers to the proximal end of the electrode catheter 12. If an electrical temperature sensor, such as a thermocouple, is to be used as an alternative, this sensor must be connected to the proximal end of the electrode catheter 12 using two electrical conductors. These electrical conductors are preferably metallic conductors. However, they may be implemented as so thin and may be thermally insulated so well in relation to the outside of the electrode catheter 12 that heating of this conductor 66 in the course of magnetic resonance tomography is insignificant.

In the electrode configuration shown, the tip electrode 14 is used both as a sensing electrode and also as a (unipolar) ablation electrode, while the ring electrode 16 is used exclusively as a sensing electrode. The electrical conductor 62 may thus also have smaller cross-sectional dimensions than the electrical conductor 44.

The ring electrode 16 is pushed onto the outside of the multi-lumen hose 58. In the same way, the cap-shaped tip electrode 14 is pushed onto the distal end of the multi-lumen hose 58. For contacting the particular electrodes 14 and 16, the corresponding lumens 56 and 60, respectively, have lateral openings in the area of the electrodes 14 and 16 (not shown in the figures). A peripheral depression which results externally on the electrode catheter 12 in a longitudinal section located between the two electrodes 14 and 16 is filled up using a UV-curable plastic 72. In the same way, the transition from the proximal end of the ring electrode 16 to the outer surface of the multi-lumen hose 58 is filled up with UV-curable plastic 72.

As previously described, the control wire 28 is connected at its distal end to the electrode catheter 12, so that the control wire 28 may cause a lateral deflection of the distal end section 24 of the electrode catheter 12 as an eccentrically situated tension wire. The connection of the distal end of the control or tension wire 28 to the electrode catheter 12 required for this purpose is produced by gluing the distal end of the control wire 28 to the lumen 26 in the area of the distal end of the control wire 28. For this purpose, the intermediate space between the control wire 28 and the wall of the lumen 26 is filled up with an adhesive 24. In order that this adhesive 74 remains at the location of the adhesive bond even in the uncured state, two hose sections 76 are pushed into the lumen 26 and onto the control wire 28 in such way that the hose sections 26 have a longitudinal section from one another and enclose the intended gluing point between them to form a seal.

Figure 2:
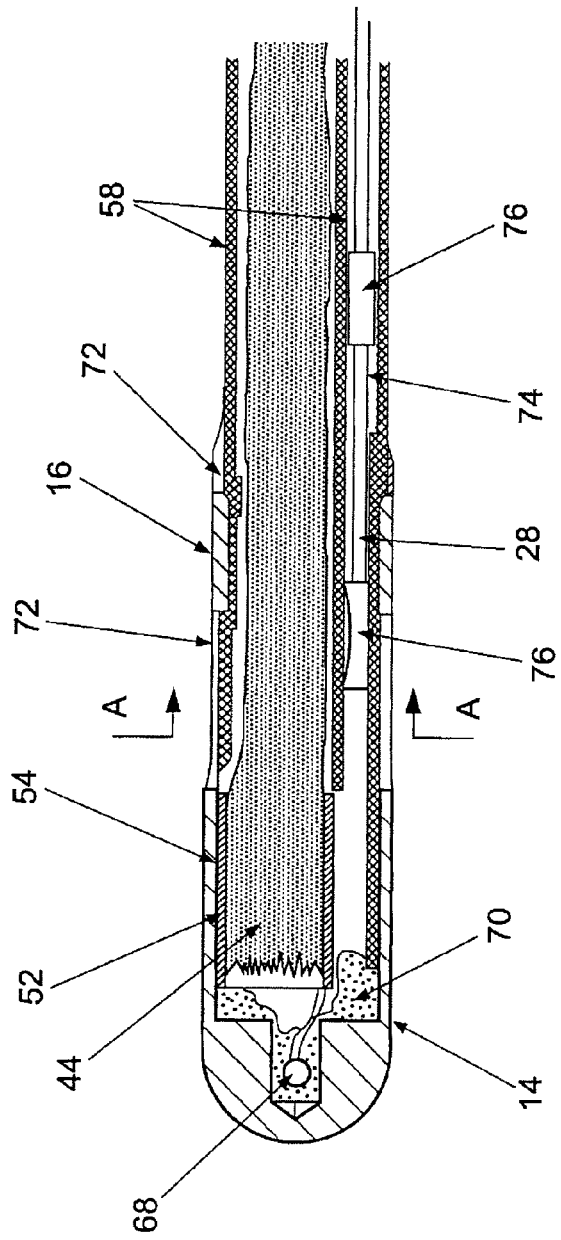
FIG. 2: shows a detail illustration of the distal end of the ablation catheter from FIG. 1 in longitudinal section.
Figure 4:
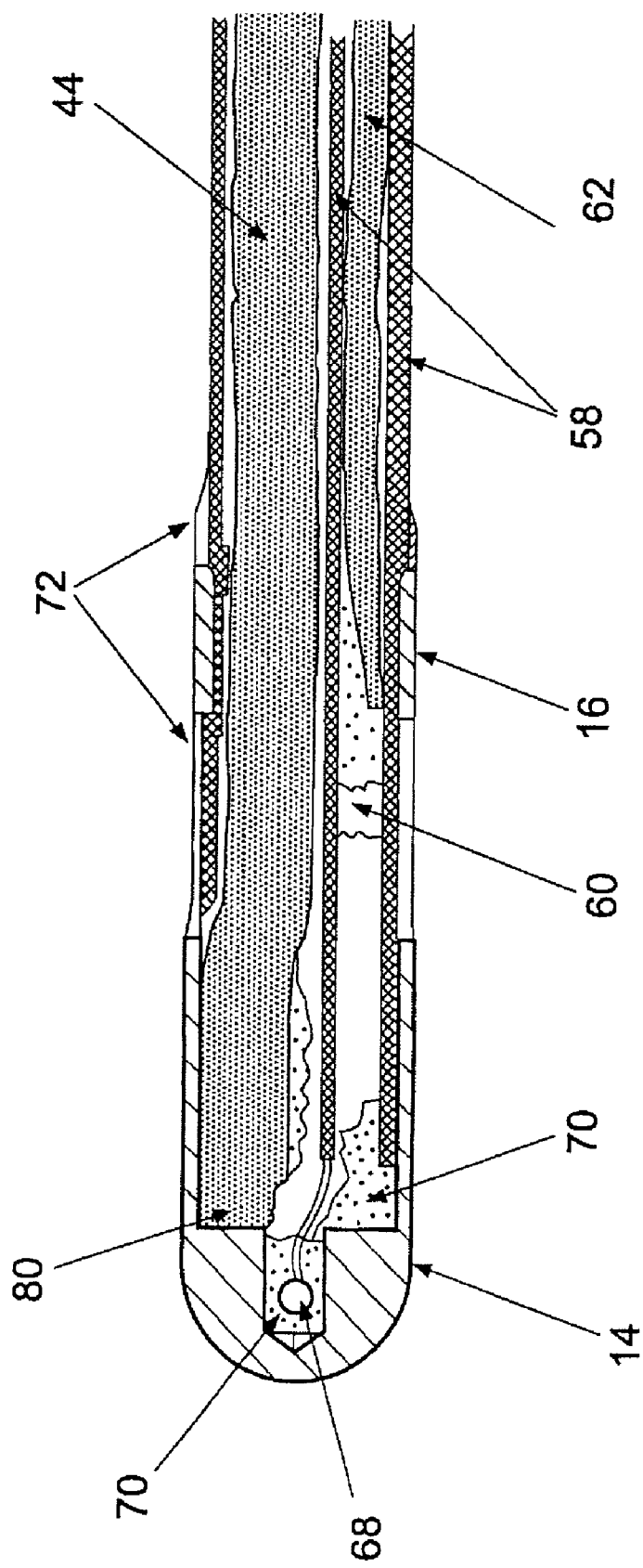
FIG. 4: shows a longitudinal section of an alternative construction of the distal end of an ablation catheter, in relation to FIG. 3, as in FIG. 1.

As noted, FIG. 4 represents an alternative construction of the distal end of the electrode catheter 12 to FIG. 2 in an enlarged illustrated longitudinal section. The embodiment variation shown in FIG. 4 differs from that shown in FIG. 2 in that the connection of the electrical conductors 44 and 62 made of carbon fibers to the corresponding electrodes 14 and 16, respectively, is not performed with the aid of crimp sleeves, but rather using an electrically conductive adhesive, using which the distal ends of the electrical conductor 62 and 44 are glued to the ring electrode 16 and the tip electrode 14, respectively. The remaining construction corresponds to that illustrated in FIG. 2.

Figure 5A:
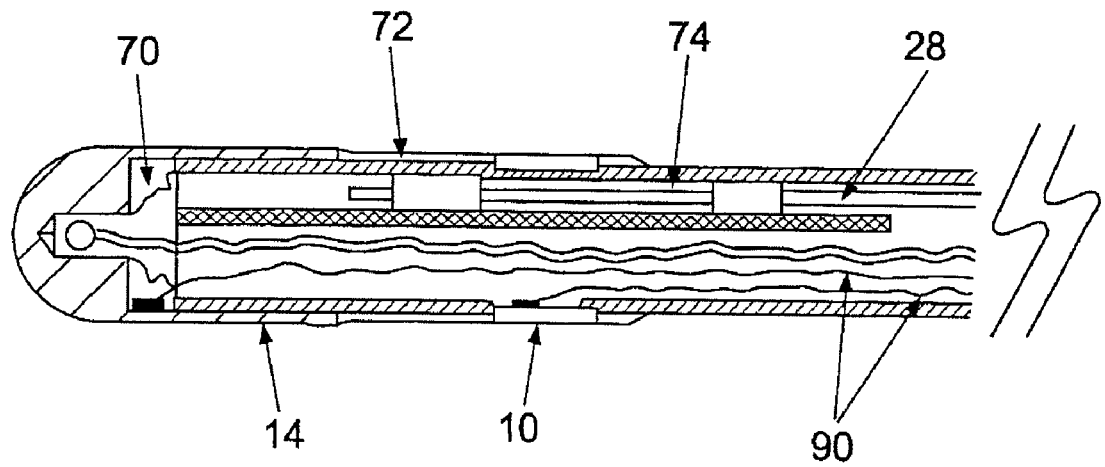
FIGS. 5a) through d): show four sequential longitudinal sections of an alternative catheter construction in longitudinal section.

FIGS. 5a) through g) show multiple longitudinal sections and cross-sections of an electrode catheter, which differs from the electrodes illustrated previously in that the electrical conductors 44 and 62 made of carbon fibers only run within the relatively inflexible, proximal longitudinal section of the electrode catheter, while the electrical conductors are typical copper conductors 90 in the flexible distal longitudinal selection of the electrode catheter, see FIGS. 5a) and 5b).

Figure 5B:
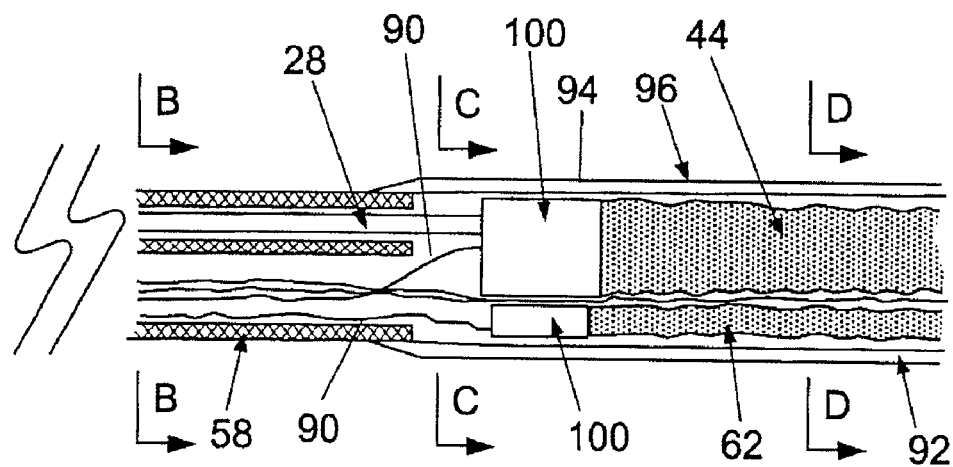
FIGS. 5e) through g): show illustrations of the cross-sections identified in FIG. 5b).

FIG. 5b) shows, in longitudinal section, the longitudinal section of the electrode catheter in which the electrode line passes from a proximal, relatively inflexible proximal shaft section to the flexible, distal shaft section. The rigidity of the proximal shaft section is caused by, inter alia, a hose-like wire braid 92, which is welded at the distal end to a metal sleeve 94 in the area of a welding point 96. The multi-lumen hose 58 is glued in the metal sleeve 94.

The conductors 44 and 62 made of carbon fibers are connected to typical copper conductors 90 both at their particular proximal ends and also at their particular distal ends. This connection is produced in the embodiment variation shown in FIG. 5 in that a particular end of the copper conductor 90 projects between the carbon fibers forming the particular electrical conductors 44 or 62, as shown in the cross-section in FIG. 5f). The copper conductor end is prevented from slipping out by a crimp sleeve 100, using which the carbon fibers of the electrical conductors 44 and 62 and the particular ends of the copper conductor 90 are squeezed together and therefore frictionally connected to one another. This type of connection between an electrical conductor made of carbon fibers and a typical metallic conductor (in particular a copper conductor) also represents an inventive idea to be implemented independently of the embodiment details described here.

The advantage of the ablation catheter variation shown in FIG. 5 over the previously described ablation catheter variations is that the flexible, distal end section of the electrode catheter has a greater flexibility due to the use of metallic conductors, in the concrete case due to the use of copper cables, and may therefore be deflected laterally better and controlled more precisely. In spite of the use of metallic conductors in the embodiment variation shown in FIG. 5, the ablation catheter shown in FIG. 5 is also suitable for magnetic resonance, since the electrical conductors have a length which is shorter than a fourth of the wavelength of a typical magnetic alternating field as is used in magnetic resonance tomography. The heating otherwise caused by a type of antenna effect of metallic electrical conductors in such alternating fields then only occurs in a very slight, insignificant amount because of the lack of tailoring.

The remaining construction of the electrode catheter shown in FIG. 5 results analogously to the exemplary embodiments described above. Accordingly, corresponding components are provided with the same reference numbers as in the preceding figures.

The invention claimed is:

1. An electrode catheter system for defibrillation or mapping or ablation of cardiac tissue, including an electrode catheter having a terminal at a proximal end of the electrode catheter and one or more sensing or treatment electrodes or both along a distal length on or in proximity to a distal end of the electrode catheter, and having at least one electrical conductor, via which the sensing or treatment electrode is electrically connected to the terminal, wherein the distal length of the electrode catheter is flexible and steerable, with the electrode catheter being more rigid proximally of the distal length, wherein the electrical conductor is made of carbon whereby the electrode catheter is constructed as capable of use in the course of magnetic resonance tomography and further wherein the electrical conductor is adapted for connection to an electrophysiology therapy device and has:
  a. at least one treatment electrode for delivering high-frequency currents for tissue ablation, and
  b. a current source connected in communication with the electrical conductor via the terminal, the current source being configured to deliver high-frequency ablating currents to the electrode.

2. The electrode catheter system according to claim 1, wherein the electrical conductor is made of carbon fibers.

3. The electrode catheter system according to claim 2, wherein the electrical conductor is enclosed by an insulating sleeve made of a flexible plastic which is compatible with magnetic resonance.

4. The electrode catheter system according to claim 3, wherein the insulating sleeve contains an x-ray contrast agent.

5. The electrode catheter system according to claim 4, wherein the x-ray contrast agent contains barium sulfate or metal particles.

6. The electrode catheter system according to claim 3, wherein the insulating sleeve is largely made of silicone.

7. The electrode catheter system according to claim 2, wherein the electrical conductor has a cross-section between 0.5 mm and 1.5 mm and a length between 40 and 120 cm.

8. The electrode catheter system according to claim 2, wherein the fibers have a diameter between 5 µm and 7 µm.

9. The electrode catheter system of claim 1 further including:
  a. a control member extending proximally from the distal length, and
  b. a handle connected to the control member,
  wherein manipulation of the handle transmits force along the control member to cause bending of the distal length.

10. The electrode catheter system according to claim 1, wherein a metallic conductor is interposed in electrical communication between the carbon electrical conductor and the electrode, the metallic conductor having shorter length than the carbon electrical conductor.

11. An electrode catheter system for ablation of cardiac tissue, including an electrode catheter, the electrode catheter extending between an at least substantially rigid proximal handle section and a flexible distal insertion section, comprising:
  a. an electrical terminal connected to the proximal handle section;
  b. two or more spaced external electrodes on the distal insertion section;
  c. electrically conductive carbon fibers extending between each external electrode and the electrical terminal; and
  d. a current source connected in communication with the conductive carbon fibers via the electrical terminal, the current source being configured to deliver ablating current to one or more of the electrodes.

12. The electrode catheter system of claim 11 wherein:
  a. a first one of the external electrodes is situated at a distal tip of the flexible distal insertion section, and
  b. a second one of the external electrodes is spaced from the distal tip of the flexible distal insertion section.

13. The electrode catheter system of claim 11 wherein the electrically conductive carbon fibers extending from a first one of the external electrodes collectively have a greater diameter than the collected electrically conductive carbon fibers extending from a second one of the external electrodes.

14. The electrode catheter system of claim 11 further comprising
  a. a temperature sensor at the distal insertion section, and
  b. at least one sensor lead extending from the temperature sensor to the proximal handle section.

15. The electrode catheter system of claim 11 wherein:
  a. a metallic conductor is in electrical communication with the electrical terminal; and
  b. an end of the metallic conductor extends adjacent ends of the electrically conductive carbon fibers extending from a first one of the external electrodes, with a sleeve surrounding and electrically engaging the end of the metallic conductor and the adjacent ends of the electrically conductive carbon fibers.

16. The electrode catheter system of claim 11 wherein the flexible distal insertion section has an x-ray contrast agent therein, whereby the flexible distal insertion section is visible by x-ray imaging.

17. The electrode catheter system according to claim 11, wherein one or more of the external electrodes has an elongated metallic conductor extending therefrom into connection with the conductive carbon fibers, with the metallic conductor having shorter length than the carbon fibers.

18. A method for electrotherapy of a heart using an electrode catheter having an electrode at or adjacent to a distal end of the electrode catheter, the electrode having electrical conductors made of carbon extending proximally therefrom, the method including the steps of:
  a. delivering high-frequency electrical currents through the electrical conductors to the cardiac tissue via the electrode, the electrical currents being of sufficient strength that they erode the cardiac tissue, and
  b. simultaneously performing magnetic resonance tomography on the cardiac tissue.

19. An electrode catheter system for use on cardiac tissue, including an electrode catheter, the electrode catheter having a length including:
  a. an at least substantially rigid proximal handle section;
  b. a flexible distal insertion section having:
    (1) two or more spaced electrodes thereon, and
    (2) a temperature sensor configured to obtain temperature reading from at least a portion of the distal insertion section;
  c. electrically conductive carbon fibers extending from the electrodes toward the handle section;
  d. an insulating sleeve extending:
    (1) about the conductive carbon fibers, and
    (2) along at least a portion of the length of the catheter, the insulating member containing an x-ray contrast agent;
  e. a control member extending from the distal insertion section toward the handle section, wherein tension on the control member flexes the distal insertion section to change the orientation of at least one of the electrodes thereon;
  f. a current source connected in communication with the conductive carbon fibers, the current source being configured to deliver ablating current to one or more of the electrodes.

20. The electrode catheter system according to claim 19, wherein one or more of the electrodes has an elongated metallic conductor extending therefrom within the distal insertion section, the conductor being:
  a. in electrical communication with, and
  b. shorter than,
  the conductive carbon fibers.

* * * * *